(12) United States Patent
Chen et al.

(10) Patent No.: US 6,671,533 B2
(45) Date of Patent: Dec. 30, 2003

(54) SYSTEM AND METHOD FOR MAPPING AND ABLATING BODY TISSUE OF THE INTERIOR REGION OF THE HEART

(75) Inventors: Peter C. Chen, Irvine, CA (US); Alan de la Rama, Cerritos, CA (US); Cary Hata, Tustin, CA (US)

(73) Assignee: Irvine Biomedical Inc., Irvine, CA (US)

( * ) Notice: Subject to any disclaimer, the term of this patent is extended or adjusted under 35 U.S.C. 154(b) by 0 days.

(21) Appl. No.: 09/975,269

(22) Filed: Oct. 11, 2001

(65) Prior Publication Data

US 2003/0073891 A1 Apr. 17, 2003

(51) Int. Cl.[7] ................................................. A61B 5/04
(52) U.S. Cl. ..................... 600/374; 600/381; 606/27; 606/41
(58) Field of Search ..................... 606/41, 42, 46, 606/47, 27, 33; 607/101, 102, 122; 600/373, 374, 585, 381

(56) References Cited

U.S. PATENT DOCUMENTS

| | | | |
|---|---|---|---|
| 5,738,683 A | 4/1998 | Osypka | |
| 5,836,947 A | 11/1998 | Fleischman et al. | |
| 5,860,920 A | 1/1999 | McGee et al. | |
| 5,885,278 A | 3/1999 | Fleischman | |
| 5,891,136 A | 4/1999 | McGee et al. | |
| 6,071,274 A | 6/2000 | Thompson et al. | |
| 6,071,279 A | 6/2000 | Whayne et al. | |
| 6,071,282 A | 6/2000 | Fleischman | |
| 6,120,500 A | 9/2000 | Bednarek et al. | |
| 6,129,724 A | 10/2000 | Fleischman et al. | |
| 6,164,283 A | 12/2000 | Lesh | |
| 6,214,002 B1 | 4/2001 | Fleischman et al. | |
| 6,315,778 B1 | * | 11/2001 | Gambale et al. ............... 606/41 |
| 6,325,797 B1 | * | 12/2001 | Stewart et al. ................. 606/41 |
| 6,529,756 B1 | * | 3/2003 | Phan et al. .................. 600/374 |
| 2002/0022833 A1 | * | 2/2002 | Maguire et al. .............. 606/27 |
| 2002/0177765 A1 | * | 11/2002 | Bowe et al. ................. 600/374 |

OTHER PUBLICATIONS

Pappone et al., *Circumferential Radiofrequency Ablation of Pulmonary Vein Ostia*, Circulation (2000) 102:2619–2628.

Lin et al. *Pulmonary Vein Morphology in Patients with Paroxylsmal Atrial Fibrillation Initiated by Ectopic Beats Orginating from the Pulmonary Veins*, Circulation, (2000) 101:1274–1281.

Natale et al. *First Human Experience with Pulmonary Vein Isolation Using a Through–the–Balloon Circumferential Ultrasound Ablation Syusytem for Recurrent Atrial Fibrillation*, Circulation, (2000) 102:1879–1882.

* cited by examiner

Primary Examiner—Lee Cohen
(74) Attorney, Agent, or Firm—Raymond Sun

(57) ABSTRACT

A catheter for sensing electrical events about a selected annulus region of the heart and for treating tissue in the selected annulus region has a handle assembly, and a shaft having a proximal end coupled to the handle assembly. The catheter also has a mapping element provided adjacent its distal end, and an ablation element positioned spaced apart along the shaft from the mapping element. The mapping element is first positioned at the desired treatment location in the selected annulus region and the desired treatment location is mapped. The ablation element is then positioned at the desired treatment location by moving the mapping element away from the desired treatment location, and the desired treatment location is ablated.

11 Claims, 8 Drawing Sheets

SECTION B-B

SYSTEM AND METHOD FOR MAPPING AND ABLATING BODY TISSUE OF THE INTERIOR REGION OF THE HEART

BACKGROUND OF THE INVENTION

1. Field of the Invention

The present invention is directed to systems and methods for mapping and ablating body tissue of the interior regions of the heart for treating cardiac conditions.

2. Description of the Prior Art

Atrial fibrillation (AF) is a common cardiac arrhythmia associated with significant morbidity and mortality. A number of clinical conditions may arise from irregular cardiac functions and the resulting hemodynamic abnormalities associated with AF, including stroke, heart failure and other thromboembolic events. AF is a significant cause of cerebral stroke, wherein the fibrillating motion in the left atrium induces the formation of thrombus. A thromboembolism is subsequently dislodged into the left ventricle and enters the cerebral circulation where stroke may result.

For many years, the only curative treatment for AF has been surgical, with extensive atrial incisions used to compartmentalize the atrial mass below that critical for perpetuating AF. Recently, transcatheter linear radiofrequency ablation in the right or left atrium has been used to replicate surgical procedures in patients with paroxysmal or chronic AF. Such ablation is carried out by a catheter system that performs both mapping and ablation. With current techniques, there is still uncertainty regarding the number of lesions, the optimum ablation site, and the need for continuous lines. As a result, focal ablation has been proposed as an alternative approach, due to the belief that ectopic beats originating within or at the ostium of the pulmonary veins (PV) may be the source of paroxysmal and even persistent AF. Although successful, the technical feasibility of this technique is restricted by the difficulty in mapping the focus if the patient is in AF or has no consistent firing, the frequent existence of multiple foci causing high recurrence rates, and a high incidence of PV stenosis.

However, there are a number of drawbacks associated with the catheter based mapping and ablation systems that are currently known in the art. One serious drawback lies in the unstable positioning of the catheter inside the atrium of the heart. When a catheter is not properly stabilized, the mapping becomes difficult and inaccurate.

Another drawback is associated with certain catheter-based systems that utilize an expandable balloon that is inflated to conform to the pulmonary vein. Unfortunately, inflation of the balloon to conform to the pulmonary vein blocks blood flow to the left atrium, and such prolonged blockage can have adverse effects to the patient. Blockage of blood flow from the PV deprives the patient from receiving oxygenated blood. In addition, the blockage may be a potential source for stenosis.

Thus, there still remains a need for a catheter-based system and method that can effectively map and ablate potentials (also known as spikes) inside PVs which can induce paroxysmal AF, while avoiding the drawbacks set forth above.

SUMMARY OF THE DISCLOSURE

It is an objective of the present invention to provide a system and method that effectively maps and ablates potentials inside the PV.

It is another objective of the present invention to provide a system and method that effectively maps and ablates potentials inside the PV without blocking blood flow.

In order to accomplish the objects of the present invention, there is provided a catheter for sensing electrical events about a selected annulus region of the heart and for treating tissue in the selected annulus region. The catheter has a handle assembly, and a shaft having a proximal end coupled to the handle assembly, a mapping element provided adjacent its distal end, and an ablation element positioned spaced apart along the shaft from the mapping element. The mapping element is first positioned at the desired treatment location in the selected annulus region and the desired treatment location is mapped. The ablation element is then positioned at the desired treatment location by moving the mapping element away from the desired treatment location, and the desired treatment location is ablated.

DETAILED DESCRIPTION OF THE PREFERRED EMBODIMENTS

Figure 1:
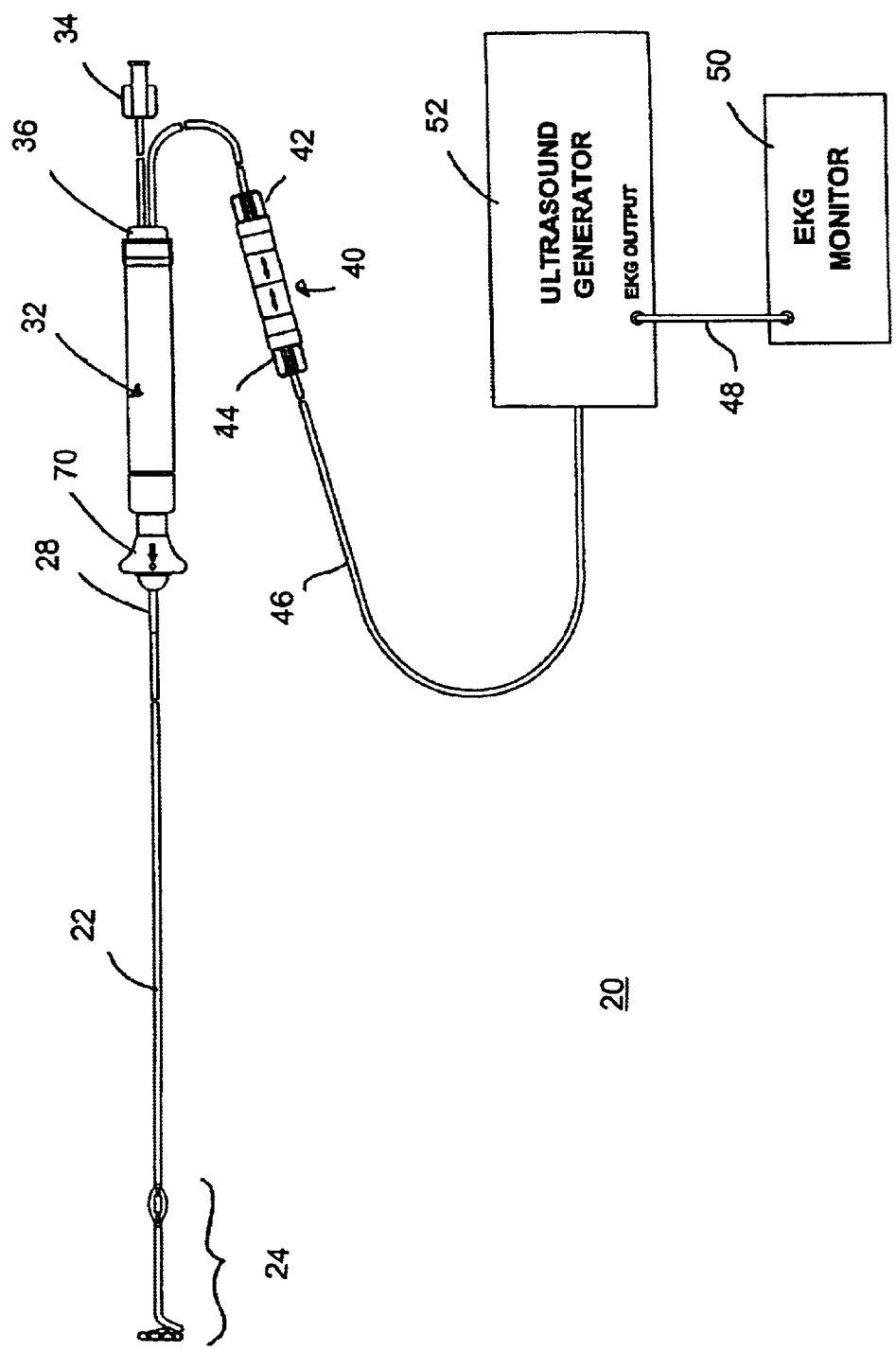
FIG. 1 illustrates a mapping and ablation system according to one embodiment of the present invention.
Figure 2:
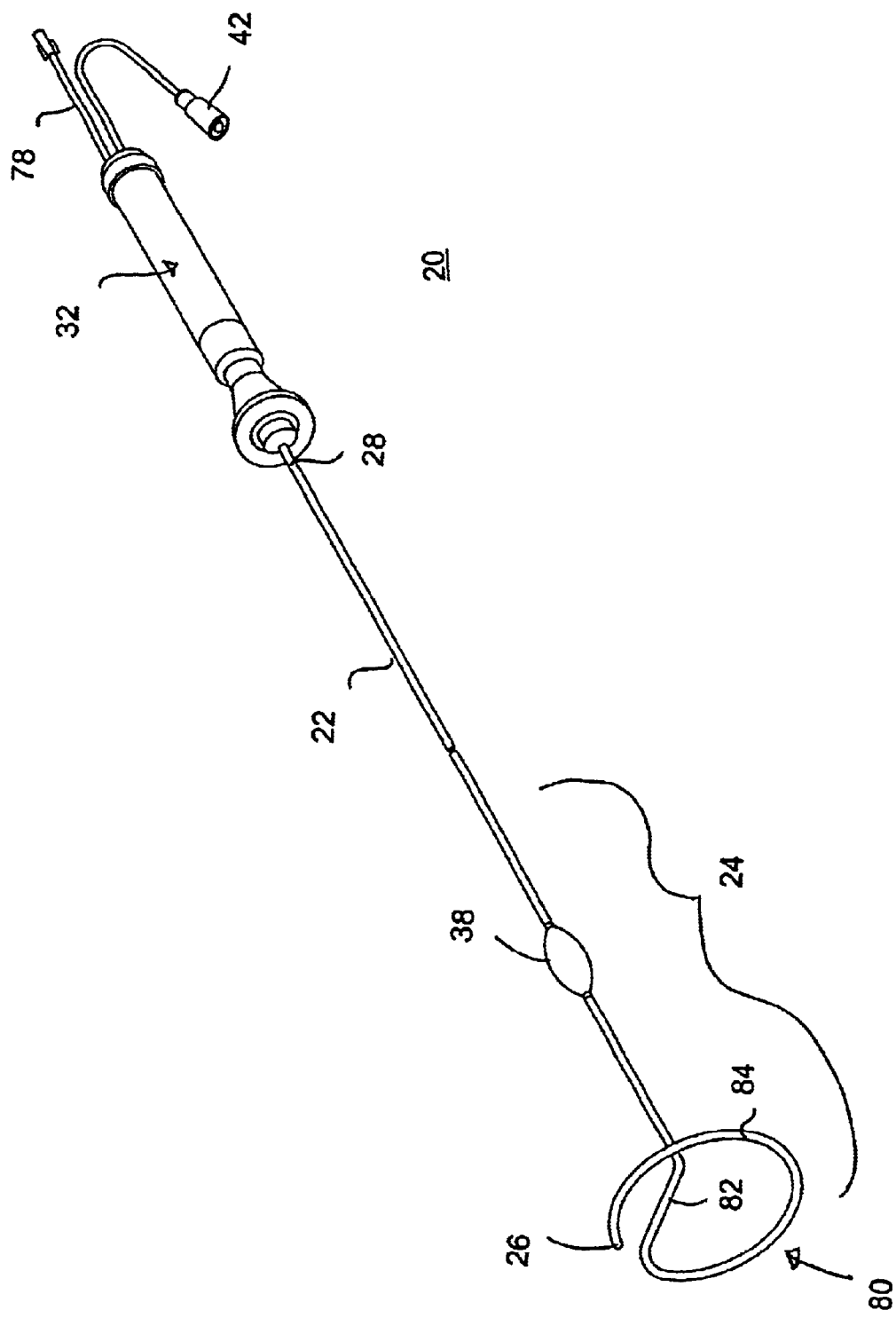
FIG. 2 is a perspective view of the catheter of the system of FIG. 1.
Figure 3:
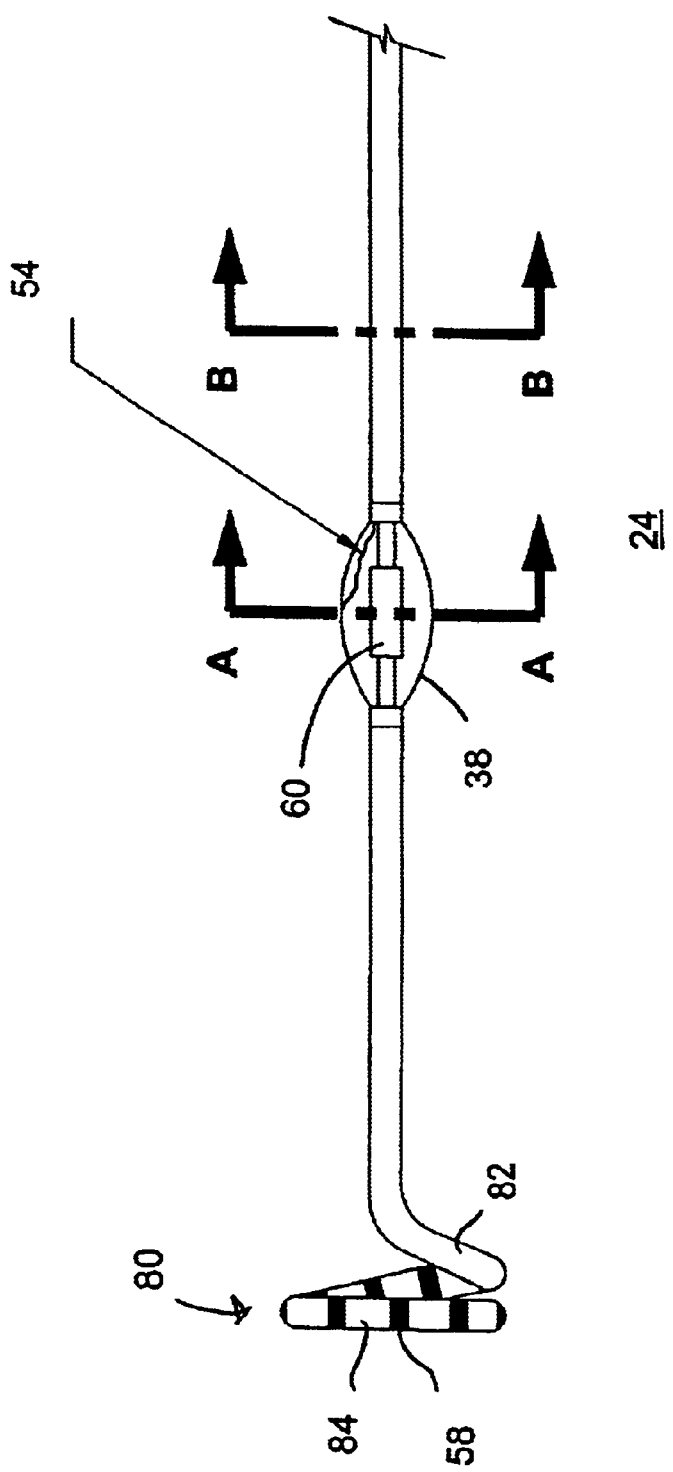
FIG. 3 is an enlarged view of the distal tip section of the catheter of FIGS. 1 and 2.
Figure 4:
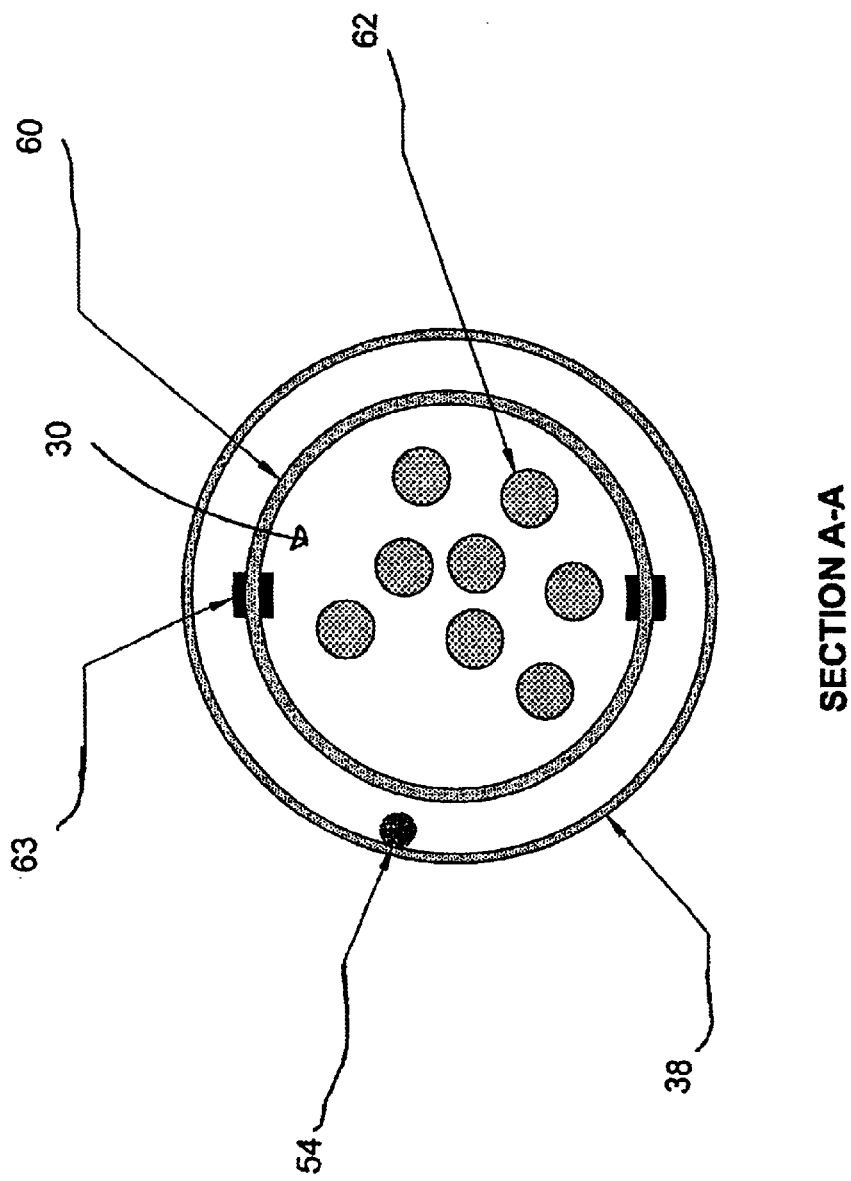
FIG. 4 is a cross-sectional view of the distal tip section of FIG. 3 taken along lines A—A thereof.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

The present invention provides a catheter system that has two separate elements for performing the mapping and ablation operations. A first element that includes ring electrodes is provided along a distal ring and functions to map the region of the heart that is to be treated. After the mapping has been completed, a second element that includes a transducer mounted inside a balloon is positioned at the location where ablation is to be performed, and is used to ablate the selected tissue. During the ablation, the distal ring functions to anchor the position of the balloon, while the balloon is inflated to a diameter that is less than the diameter of the distal ring and the annulus where the treatment is taking place. As a result, blood can still flow unimpeded through the annulus.

Even though the present invention will be described hereinafter in connection with treating AF, it is understood that the principles of the present invention are not so limited, but can be used in other applications (e.g., treatment of accessory pathways, atrial flutter, ventricular tachycardia), and in other body pathways (e.g., right atrium, superior vena cava, right ventricle, left ventricle).

FIGS. 1–8 illustrate a catheter system 20 according to one embodiment of the present invention. The catheter system 20 has a tubular shaft 22 having a distal tip section 24, a distal end 26, a proximal end 28, and at least one lumen 30 extending through the shaft 22. A handle assembly 32 is attached to the proximal end 28 of the shaft 22 using techniques that are well-known in the catheter art.

The distal tip section 24 includes an expandable balloon 38 and a distal ring 80 that makes up the distal-most end of the shaft 22. A transducer 60 (e.g., piezoelectric or ultrasound) is housed inside the balloon 38. The balloon 38 can be made from any conventional material (such as but not limited to silicone, polyurethane, latex, polyamide and polyethylene), and heat bonded or otherwise attached to the shaft 22 using techniques that are well-known in the catheter art.

The distal ring 80 can be preformed into a generally curved or circular shape, resembling an open loop. The shape of the distal ring 80 corresponds to the circumferential geometry of a selected annulus (e.g., the PV) in the heart. In fact, the preformed shape of the distal ring 80 can be provided in a variety of curved geometries to overlie the anatomical geometry of the selected annulus. The distal ring 80 includes a transition section 82 that extends distally at an angle from the longitudinal axis of the shaft 22, and has a generally open-looped circular section 84 that extends from the transition section 82. As best seen from FIG. 3, the circular section 84 is oriented at an approximately perpendicular orientation from the longitudinal orientation of the shaft 22. The distal ring 80 can be made from the same material as the shaft 22. Such a material can be an electrically nonconductive, biocompatible, resilient plastic material which retains its shape and which does not soften significantly at human body temperature (e.g., Pebax™, polyethylene or polyester). As a non-limiting example, the geometry of the distal ring 80 can be created by thermoforming it into the desired shape.

A plurality of thermocouple wires 54 can have their distal tips secured to the interior surface of the balloon 38 (see FIG. 3), and are used to detect the temperature at the treatment site.

A plurality of ring electrodes 58 are provided in spaced-apart manner about the circular section 84 of the distal ring 80. The ring electrodes 58 can be made of a solid, electrically conducting material, like platinum or gold, that is attached about the circular section 84. Alternatively, the ring electrodes 58 can be formed by coating the exterior surface of the circular section 84 with an electrically conducting material, such as platinum or gold. The coating can be applied by sputtering, ion beam deposition or similar known techniques. The number of ring electrodes 58 can vary depending on the particular geometry of the region of use and the functionality desired.

As will be explained in greater detail below, the ring electrodes 58 function to map the region of the heart that is to be treated. After the mapping has been completed, the balloon 38 is positioned at the location where ablation is to be performed, and the distal ring 80 functions to anchor the position of the balloon 38. The balloon 38 is expanded, but even the greatest expanded diameter of the balloon 38 will be provided to be less than the diameter of the distal ring 80 when the distal ring 80 is fully deployed (see FIGS. 2, 3 and 7). The ablation is then carried out by energy that is emitted from the ultrasound transducer 60 through the inflation media (e.g., fluid, saline, contrast media or mixture) inside the balloon 38, and the balloon 38 itself.

A standard Luer fitting 34 is connected to the proximal end 36 of the handle assembly 32 using techniques that are well-known in the catheter art. The Luer fitting 34 provides a fluid line for inflation media to be introduced to inflate the balloon 38 at the distal tip section 24 of the shaft 22. The inflation media is delivered via an inflation lumen 76 that extends from the handle assembly 32 (and coupled to the line 78 of the Luer fitting 34), and terminates at the balloon 38.

A connector assembly 40 is also connected to the proximal end 36 of the handle assembly 32 using techniques that are well-known in the catheter art. The connector assembly 40 has a proximal connector 42 that couples the handle assembly 32 to the connector 44 of a control line 46 that leads to an ultrasound generator 52. An EKG monitor 50 is coupled to the ultrasound generator 52 via another line 48. The EKG monitor 50 can be a conventional EKG monitor which receives (via the ultrasound generator 52) electrical signals detected by the ring electrodes 58 at the distal tip section 24, and processes and displays these electrical signals to assist the physician in locating the site of potentials in a PV. The ultrasound generator 52 can be a conventional ultrasound generator that creates and transmits ablating energy to the ultrasound transducer 60 that is positioned inside the balloon 38. The ultrasound transducer 60 will emit the energy to ablate the tissue that extends radially from the position of the balloon 38.

Electrical wires (not shown) extend from the ultrasound generator 52 along the lines 46 and 48, and conductor wires 62 and ultrasound wires 63 extend through the connector assembly 40, the handle assembly 32 and the lumen 30 of the shaft 22 to the distal tip section 24 of the shaft 22 to couple the ring electrodes 58 and the transducer 60, respectively. In addition, the thermocouple wires 54 can extend from the balloon 38 through the lumen 30 of the shaft 22 and the handle assembly 32 to the proximal connector 42, where they can be electrically coupled by the wires in the line 46 to the ultrasound generator 52 where the temperature can be displayed.

Figure 5:
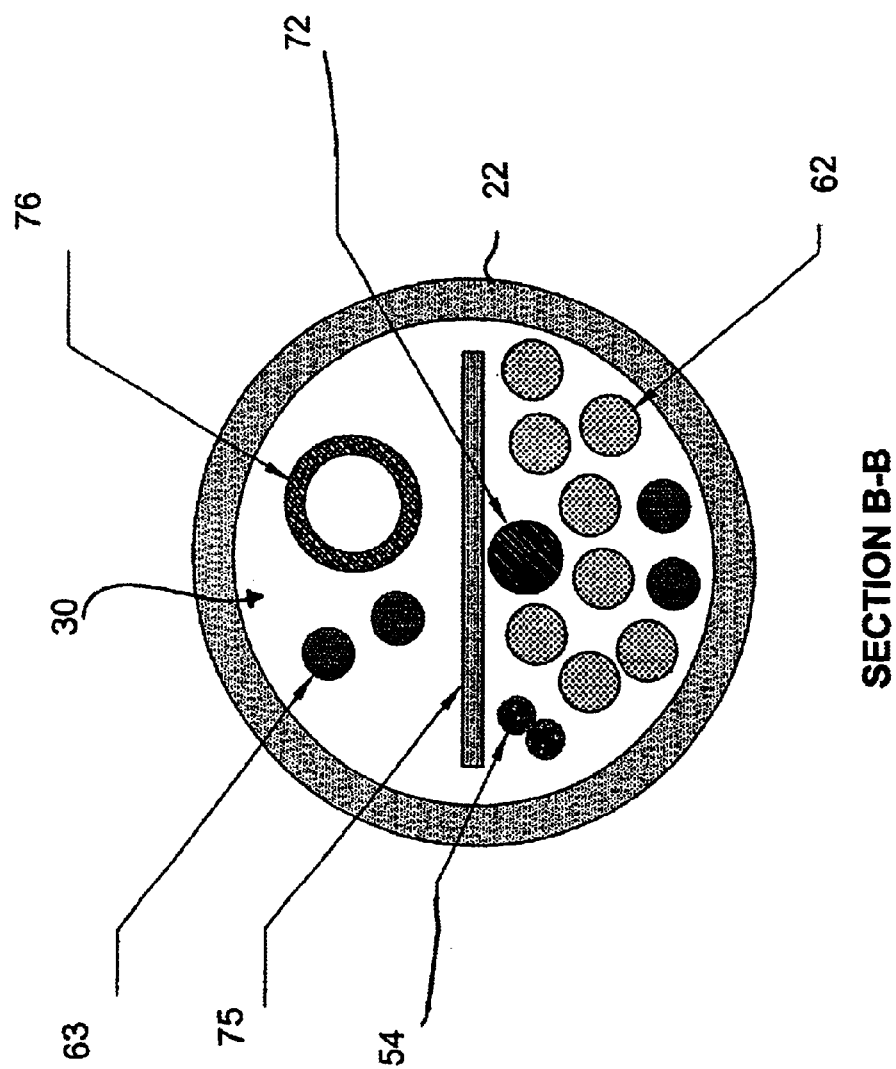
FIG. 5 is a cross-sectional view of the distal tip section of FIG. 3 taken along lines B—B thereof.
Figure 8:
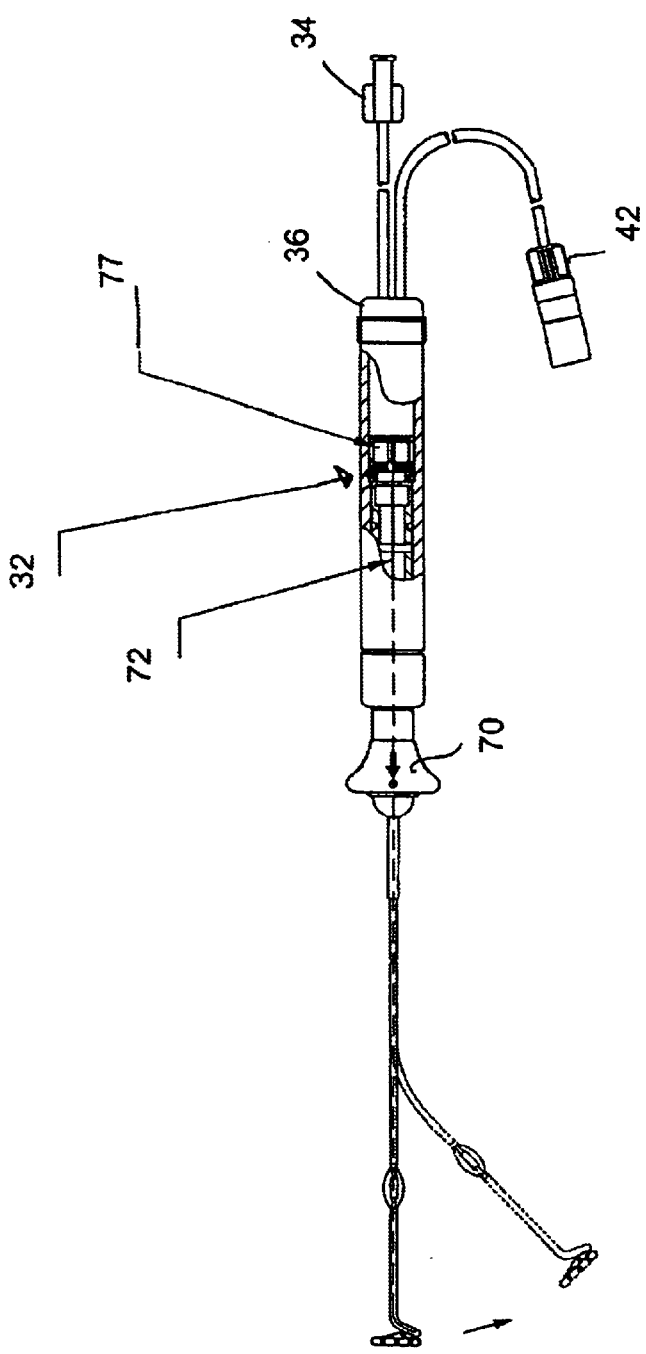
FIG. 8 illustrates the steering mechanism of the catheter of FIGS. 1 and 2.

The handle assembly 32 also includes a steering mechanism 70 that functions to deflect the distal tip section 24 of the shaft 22 for maneuvering and positioning the distal tip section 24 at the desired location in the heart. Referring to FIGS. 1, 5 and 8, the steering mechanism 70 includes a steering wire 72 that extends in the main lumen 30 of the shaft 22 from its proximal end at the handle assembly 32 to its distal end which terminates in the distal tip section 24 before the location of the balloon 38. The proximal end of the steering wire 72 is wound around or secured to an anchor 77 that is fixedly positioned inside the handle assembly 32. The steering mechanism 70 also includes a flat wire 75 that extends in the lumen 30 from the anchor 77 to its distal end at a location slightly proximal to the balloon 38 (as shown in FIG. 5). The flat wire 75 is attached to the steering wire 72 at the distal ends of the flat wire 75 and the steering wire 72 so as to be controlled by the steering wire 72. Specifically, by pushing the steering mechanism 70 forward in a distal direction, the steering mechanism 70 will pull the steering wire 72 in a proximal direction, causing the distal tip section 24 to deflect to one direction (see in phantom in FIG. 8). By pulling back the steering mechanism 70 in a proximal direction, the steering wire 72 is deactivated and the distal tip section 24 returns to its neutral position or deflects to the opposite direction.

The distal ring 80 can be preformed to a fixed size (i.e., diameter) and shape that cannot be changed. Alternatively, the diameter of the distal ring 80 can be adjusted using techniques and incorporating mechanisms that are well-known in the catheter art.

Figure 6:
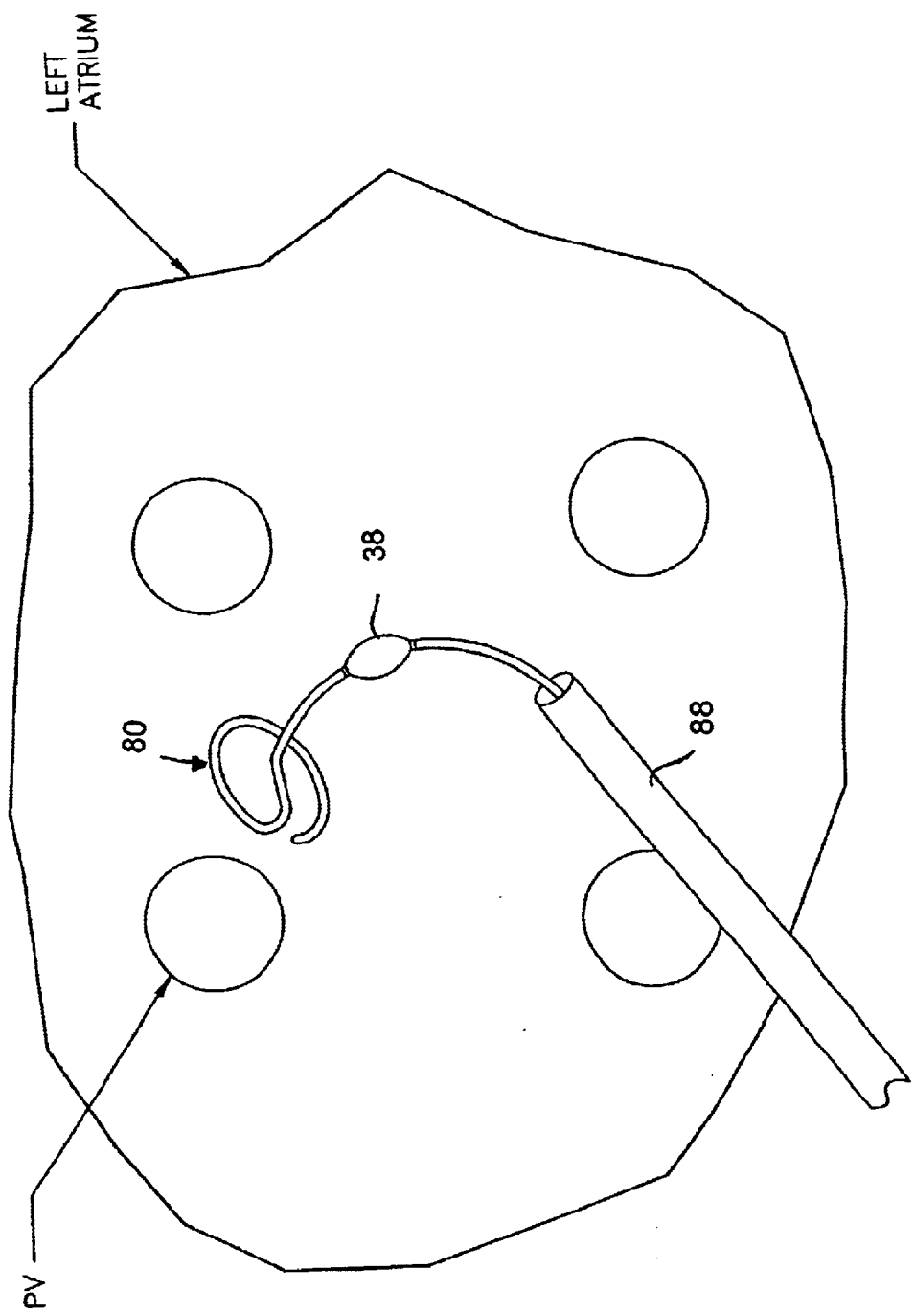
FIG. 6 illustrates how the catheter of FIGS. 1 and 2 is deployed for use inside the heart of a patient.
Figure 7:
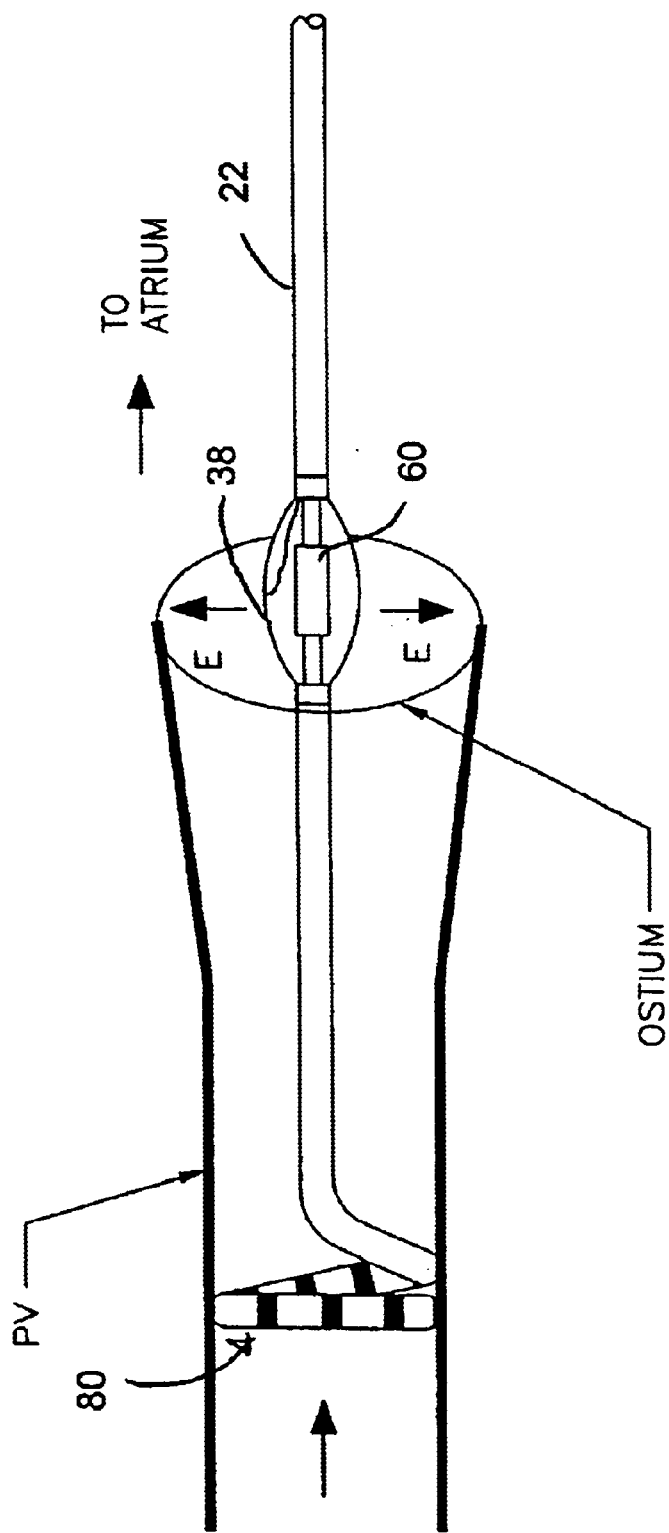
FIG. 7 is a cross-sectional view illustrating the catheter of FIGS. 1 and 2 in use in a pulmonary vein during the mapping and ablation steps.

FIGS. 6 and 7 illustrate how the catheter system 20 is used. First, a guide sheath 88 is provided to deliver the shaft 22 and distal ring 80 to the desired location (e.g., the left atrium) in the heart. The shaft 22 is slid into the hollow lumen of the guide sheath 88, and the guide sheath 88 can slide forward and backward along the longitudinal axis of the shaft 22. When the guide sheath 88 is slid forwardly towards the distal ring 80, the distal ring 40 is progressively straightened out and drawn into the lumen of the guide sheath 88. Thus, when confined with the guide sheath 88, the distal ring 80 assumes the generally linear low profile shape of the guide sheath 88, which allows a physician to employ conventional percutaneous access techniques to introduce the catheter 20 into a selected region of the heart through a vein or artery. When the guide sheath 88 is slid rearwardly away from the distal ring 80, the distal ring 80 is uncovered and its resilient memory will cause the distal ring 80 to re-assume its preformed generally circular shape.

To introduce and deploy the distal tip section 24 within the heart, the physician uses a conventional introducer to establish access to a selected artery or vein. With the guide sheath 88 confining the distal ring 80, and with the balloon 38 deflated, the physician introduces the shaft 22 and the guide sheath 88 through a conventional hemostatic valve on the introducer and progressively advances the guide sheath 88 through the access vein or artery into the desired atrium, such as the left atrium as shown in FIG. 6. The physician observes the progress of the guide sheath 88 using fluoroscopic or ultrasound imaging. The guide sheath 88 can include a radio-opaque compound, such as barium, for this purpose. Alternatively, radio-opaque markers can be placed at the distal end of the guide sheath 88.

The shaft 22 and the guide sheath 88 can be maneuvered to the left atrium by the steering mechanism 70. Once located in the left atrium, the physician slides the guide sheath 88 back to free the distal ring 80 which resiliently returns to its preformed shape. The distal ring 80 is then maneuvered into contact with the selected annulus (e.g., the ostium) with the aid of fluoroscopy. Good contact is established when the ring electrodes 58 contact the selected annulus, and at this time, the physician operates a control located on the ultrasound generator 52 to effectuate the mapping of the selected annulus by the ring electrodes 58. The results of the mapping operation are processed and displayed at the EKG monitor 50. A differential input amplifier (not shown) in the EKG monitor 50 processes the electrical signals received from the ring electrodes 58 via the wires 62, and converts them to graphic images that can be displayed. The thermocouple wires 54 can also function to monitor the temperature of the surrounding tissue, and provide temperature information to the ultrasound generator 52. Throughout this mapping operation, the balloon 38 remains deflated.

Once the mapping operation has been completed, the distal tip section 24 is maneuvered forward so that the balloon 38 can be positioned at the desired treatment location (e.g., the PV in FIG. 7). Once the desired position of the balloon 38 has been confirmed, the physician can then inflate the balloon 38 using inflation media. The balloon 38 is preferably manufactured using known techniques to a predetermined diameter so that its diameter at its maximum expansion will be less than the diameter of the distal ring 80 and the annulus or vessel (e.g., the PV in FIG. 7) where the ablation is to take place. The physician then controls the ultrasound generator 52 to generate ultrasound energy that is propagated through the wires 63 to the ultrasound transducer 60 that is positioned inside the balloon 38. The energy radiates in a radial manner from the transducer 60, propagates through the inflation media (which acts as an energy transmitting medium) inside the balloon 38, exits the balloon 38 and then reaches the selected tissue (typically in a waveform) to ablate the tissue. See the arrows E in FIG. 7 which illustrate the radiation of the energy from the transducer 60.

During the ablation, the distal ring 80 functions to anchor the distal tip section 24 inside the PV at the desired location so that the ablation can be performed accurately. In contrast to known catheter systems where the same element is used to anchor and ablate, by providing a separate element (i.e., the distal ring 80) to anchor the distal tip section 24, the function of the ablation element (i.e., the balloon 38 and transducer 60) will not be affected by the anchoring device, thereby ensuring that the ablation is performed accurately and effectively. In addition, since the maximum diameter of the balloon 38 is always smaller than the smallest diameter of the distal ring 80, blood will be able flow through the distal ring 80 and around the surfaces of the balloon 38.

When the ablation has been completed, the balloon 38 is deflated and the distal tip section 24 withdrawn from the heart.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A catheter for sensing electrical events about a selected annulus region of the heart and for treating tissue in the selected annulus region, comprising:

a handle assembly;

a shaft having a proximal end coupled to the handle assembly, and a distal end, the shaft extending along an axis;

a distal ring provided at the distal end and oriented perpendicular to the axis of the shaft, the distal ring having a plurality of electrodes positioned in spaced-apart manner about the distal ring;

an ablation element positioned spaced apart from the distal ring an expandable member covering the ablation element; and wherein the distal ring has a diameter that is greater than the fully expanded diameter of the expandable member.

2. The catheter of claim 1, wherein the ablation element emits energy to a radially surrounding area.

3. The catheter of claim 2, wherein the shaft has a main lumen, and further including a plurality of wires that are coupled to the ablation element and extending through the main lumen.

4. The catheter of claim 1, wherein the expandable member defines an interior space that is filled with a fluid.

5. The catheter of claim 1, wherein the shaft has a main lumen, and further including a plurality of wires that are coupled to the plurality of electrodes and extending through the main lumen.

6. The catheter of claim 1, wherein the shaft has a main lumen, and further including a steering mechanism that includes a steering wire extending through the main lumen to the distal end.

7. The catheter of claim 1, wherein the shaft has a main lumen, and further including a plurality of thermocouple wires that are coupled to the distal end and extending through the main lumen.

8. A system for sensing electrical events about a selected annulus region of the heart and for treating tissue in the selected annulus region, comprising:
- a catheter having:
  - a handle assembly;
  - a shaft having a proximal end coupled to the handle assembly, and a distal end, the shaft extending along an axis;
  - a distal ring provided at the distal end and oriented perpendicular to the axis of the shaft, the distal ring having a plurality of electrodes positioned in spaced-apart manner about the distal ring; and
  - an ablation element positioned spaced apart from the distal ring;
- an expandable member covering the ablation element;
- an energy source coupled to the ablation element; and
- means coupled to the plurality of electrodes for processing electrical signals received from the plurality of electrodes;

wherein the distal ring has a diameter that is greater than the fully expanded diameter of the expandable member.

9. A method of ablating tissue in a body cavity, comprising: providing a catheter having a shaft having a proximal end and a distal end, with the distal end of the shaft having a distal ring that has a plurality of mapping electrodes, and an ablation element that is separate and spaced apart from the distal ring;
- positioning the distal ring at the desired treatment location in the body cavity;
- mapping the desired treatment location;
- positioning the ablation element at the desired treatment location by moving the distal ring away from the desired treatment location;
- ablating the desired treatment location;
- wherein the ablation element is provided in the form of a transducer housed inside an expandable element; and
- expanding the expandable element to a maximum diameter that is less than the smallest diameter of the distal ring.

10. The method of claim 9, further including:
anchoring the distal ring in the body cavity.

11. The method of claim 9, wherein the step of ablating the desired treatment location includes emitting energy to the desired treatment location.

* * * * *